128-716 SR
10/7/86 OR H 000,145

United States Statutory Invention Registration [19]

[11] Reg. Number: H145
[43] Published: Oct. 7, 1986

James

[54] RESEARCH APPARATUS

[75] Inventor: John T. James, Severn, Md.

[73] Assignee: The United States of America as represented by the Secretary of the Army, Washington, D.C.

[21] Appl. No.: 633,569

[22] Filed: Jul. 23, 1984

[51] Int. Cl.[4] ..... A61B 5/08
[52] U.S. Cl. ..... 128/716; 128/204.23; 128/720; 128/725
[58] Field of Search ..... 128/716, 724, 1 B

[56] References Cited

U.S. PATENT DOCUMENTS 3,976,053 8/1976 Reininghaus ..... 128/724
4,221,211 9/1980 Brasch ..... 128/1 B
4,402,315 9/1983 Tsuda et al. ..... 128/716 X

*Primary Examiner*—Harold J. Tudor
*Attorney, Agent, or Firm*—Anthony T. Lane; Harold H. Card, Jr.; Michael C. Sachs

[57] ABSTRACT

A 75-liter plexiglass chamber has been constructed to simultaneously expose 10 rats to a test vapor. Each rat is confined in a small plexiglass plethysmographic box attached to the large chamber. During exposure, the respiration rate, tidal volume, body temperature, pH, and blood gases are measured. A sample of the blood may be used to measure the amount of a volatile test chemical reaching the blood or to measure blood $pCO_2$, $pO_2$, and pH. This apparatus optimizes animal usage by permitting many sequential measurements on a minimum number of test animals. Since the animals are exposed simultaneously, the interanimal variations in exposure are minimized.

1 Claim, 4 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

RESEARCH APPARATUS

GOVERNMENT RIGHTS

The invention described herein may be manufactured, used and licensed by the Government for Governmental purposes without the payment to me of any royalties thereon.

BACKGROUND OF THE INVENTION

1. Field of Use

This invention relates to a research apparatus for use in measuring the various physical and chemical responses of small mammals to inhaled gaseous chemicals.

More particularly, this invention relates to a research apparatus for use in the simultaneous measurement of body temperature, blood gases, respiratory rates, and tidal volume of mammals which are responsive to the inhalation of gaseous chemicals.

2. Description of Prior Art

A question exists as to whether damage to the respiratory system has occurred on test animals as the result of subchronic exposure to a test chemical. In the past, the question was indirectly answered by histopathological, physiological and lavage studies of the lungs. However, these techniques cannot determine whether the respiratory system is still capable of its primary function, viz. efficient exchange of $O_2$ and $CO_2$ between air and pulmonary blood.

Another question concerns the immediate respiratory response of a test animal during an acute exposure to a test vapor. One would like to measure the respiratory rate, tidal volume, blood gases, concentration of vapor in the blood, and metabolites present in the blood. The apparatus of this invention provides a way for state of the art methodology to answer these questions in mammals, particularly rats.

SUMMARY OF INVENTION

It is therefore an object of this invention to provide a research apparatus which may be used to simultaneously study the biochemical and physiological responses of a mammal to the inhalation of a test chemical.

Another object is to provide an apparatus which may be used to evaluate the respiratory function of mammals following subchronic exposure to a test chemical.

A further object is to provide an apparatus which may be used in conjunction with state of the art methodology to measure the respiratory rate, tidal volume, body temperature, and blood components on mammals exposed to a test chemical.

Other objects and the attendant advantages thereof will become more apparent from the detailed description taken with the drawings wherein.

Figure 1:
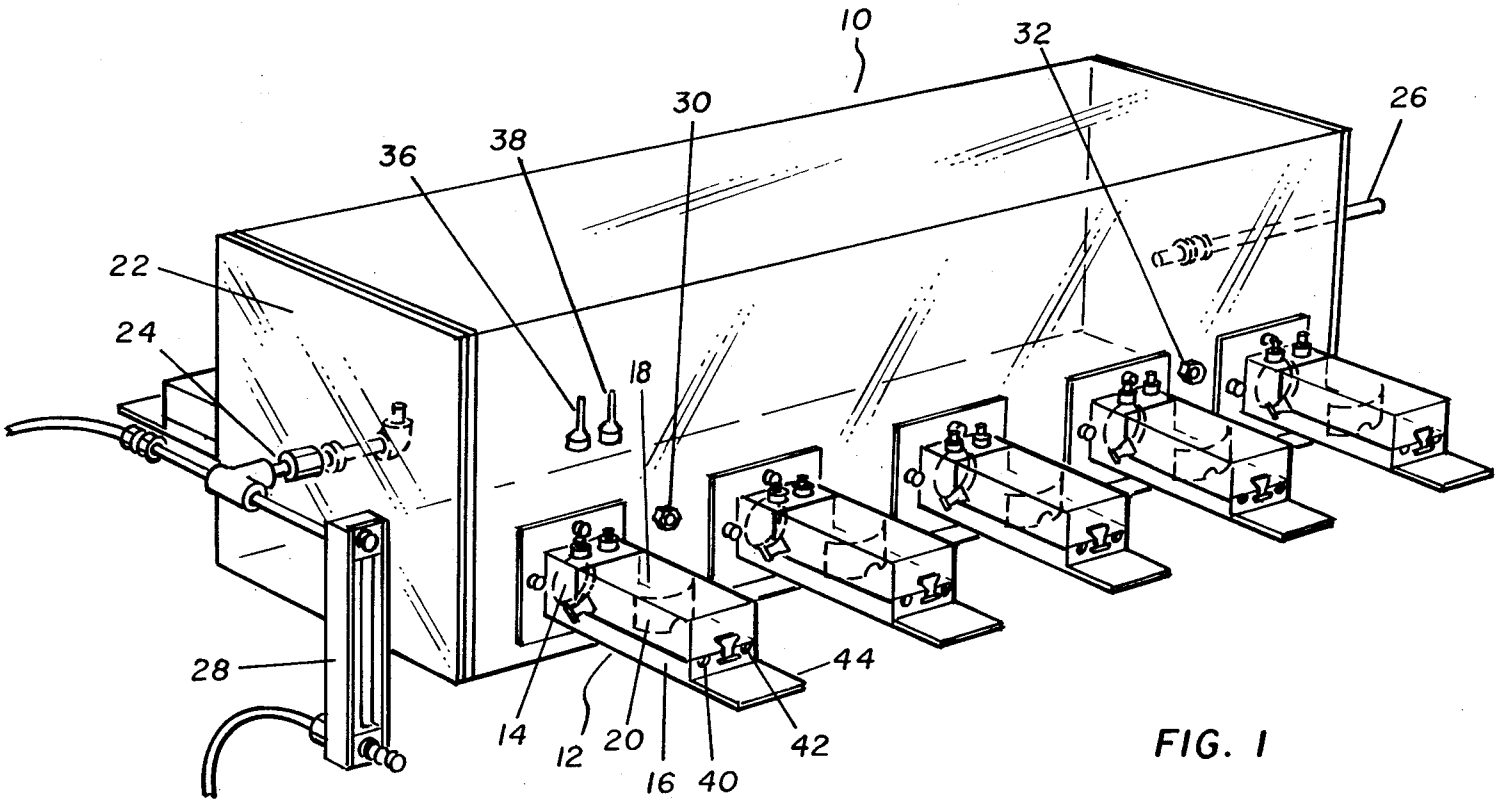
FIG. 1 is a view showing the apparatus of this invention.
Figure 2:
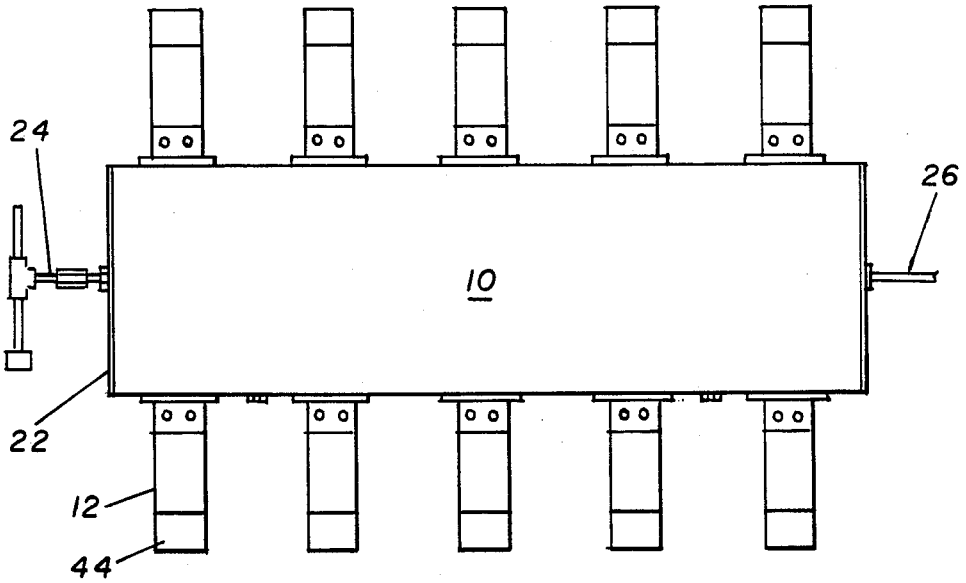
FIG. 2 is a top plan view showing the present apparatus.
Figure 3:
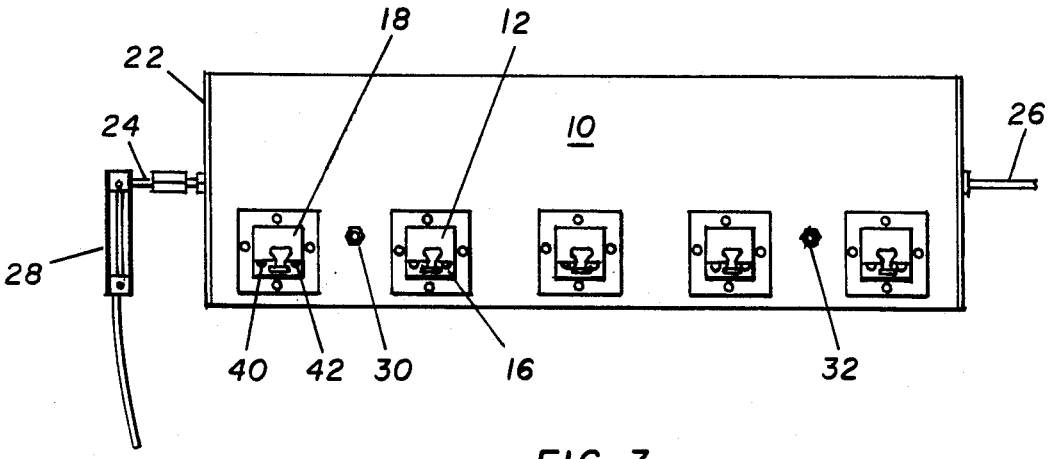
FIG. 3 is a view showing the apparatus of FIG. 2.
Figure 4:
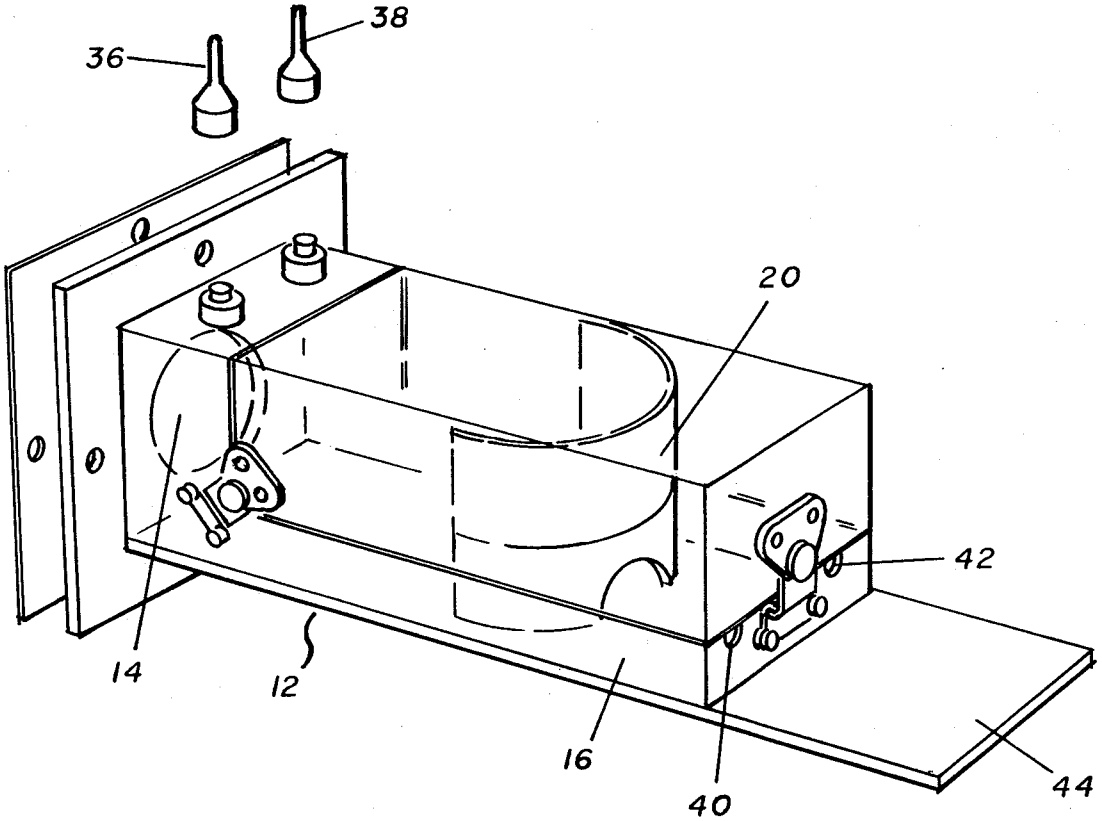
FIG. 4 is a view showing the individual cells of this invention.

Utilizing the present apparatus, the ability of the respiratory system to maintain normal $pO_2$ and $CO_2$ in blood may be measured on arterial samples obtained anaerobically from an unexcited and unanesthesized rat. This has been attempted for about two decades with limited success. It has never been accomplished on more than one rat at a time. Limitations to previous approaches have been the large volume of blood required, the location of the arterial cannula, the time required to do rats individually, or the failure to provide for variations on $O_2$ and $CO_2$ in the inspired air. This apparatus overcomes each of these limitations when used as described herein.

As for the art, the objective is to optimize the amount of useful data obtained on a minimum number of experimental animals. The apparatus described enables blood sampling and plethysmographic measurements to be done simultaneously. Thus one can investigate the ability of the test vapor to penetrate the air-blood barrier, the response of the respiratory system to that vapor, and the impact the response has on blood gases and pH. The capability of observing these parameters simultaneously is unique to this apparatus, and the ability to do this type research on several rats at one time is particularly unique to this apparatus.

DESCRIPTION OF THE PREFERRED EMBODIMENT

In general, referring to the drawings, the apparatus of this invention is provided with a main chamber of closed construction having inlet and outlet means for a test gaseous chemical. The main chamber 10 is provided with 10 plethysmographic cells 12 in spaced relation along both sides of the chamber. Each of the cells are integral with the main chamber with a port 14 communicating therebetween. The individual cells are provided with a base 16 and a separably engaged cover 18. Also, the base of each of the cells is provided with an manually adjustable plate 20 to secure the mammal in position in the cell. In practice, the cover 18 is removed and the mammal is placed in the box with its head passing through the port 14 to the main chamber. The plate is adjusted to secure the mammal in position, and the cover 18 is replaced on the cell. A sealing collar may be placed around the head of the mammal which will seal and secure the port from leakage.

The main chamber 10 is constructed of $\frac{3}{8}$ inch plexiglas with internal dimensions of $28 \times 28 \times 96$ cm. The test vapor enters at one end 22 through a $\frac{3}{8}$ inch circular elbow 24 and leaves through a similar opening 26 in the other end. The proportion of each gas whether it be air, nitrogen, or carbon dioxide is regulated by a series of rotameters 28. Room air is pumped with an oil-less vacuum pump and other gases are delivered from cylinders. The flow rate is maintained between 18 and 35 liters per minute during experimentation. Two sampling ports 30 and 32, at the level where rats are breathing, are provided and measurements from these posts provide an accurate quantitation of the atmosphere in the chamber.

Five plethysmographic boxes 12 are bolted to each side of the main chamber. These are constructed of $\frac{1}{4}$ inch plexiglas with internal dimensions of $5 \times 5 \times 18$ cm. A 3.2 cm circular opening 14 permits the head of the rat to extend into the chamber. A thin rubber collar with a circular opening (1.8–2.2 cm diameter) forms an adequate seal around the neck area. Two Luer-Lok syringe tips 36 and 38 are glued over 1/16 inch holes in each box. One tip 36 is used for sensing pressure changes during respiration and the other 38 may be connected to a syringe for calibration of the volume response of the transducer. The top portion 18 of the box 12 is removable for entry of the rat. Once the rat is in place, a rear restrainer in the form of an adjustable plate 20, which is movable to accomodate different sizes of rats, ensures that the rat cannot back out of the main chamber. Notches 40 and 42 are provided for exit of catheter and rectal temperature probe. The bottom 16 of the box is extended to provide a platform 44 for holding the blood sampling paraphernalia.

The inhalation chamber and plethysmographic boxes of the present device allow the methodology described herein to be applied to questions of a toxicologic or pharmacologic nature. By utilizing this sytem the primary toxicologic question of whether animals, after prolonged exposure to a toxin, are capable of maintaining normal gaseous exchange between inspired air and pulmonary blood is now answered. Also, blood gas measurements on animals respiring air may be used as a screening procedure with the use of this apparatus in the evaluation of respiratory system damage. Further, in order to detect minimum respiratory dysfunction, one is able through the use of the present device to expose test animals to hypoxic and hypercapnic conditions that stress the respiratory system. Also, acceptable specimens for blood gas analysis are taken anaerobically in unanethesized animals with a minimum manipulation of the animal. Once exposure has ended, the disappearance of test chemical and its metabolites from the blood may be followed for hours utilizing the device.

Additional toxicologic information may be obtained by the measurement of respiration rate and tidal volume. Respiratory damage caused by prolonged exposure to toxins may be measured during resting respiration, or during hypoxic or hypercapnic respiration. Further, during an acute vapor exposure, these variables should indicate whether there is sensory irritation or pulmonary irritation.

I claim:

1. A gas chamber having a rectangular body provided with a top, bottom, two longitudinal sides and a first and second end, said first end having a gas inlet and said second end having a gas outlet for the longitudinal passage of said gas through said chamber and between said sides, a plurality of cells provided in longitudinal spaced relationship along each of said sides of said chamber, said cells each having a port communicating with said chamber, a base provided with a removable cover, and a manually longitudinally adjustable plate, and all said cells provided with a mammal having a head and body, said head protruding through said port and said body secured in position in said cell by said adjustable plate, each of said cells having individual means for pressure sensing, temperature sensing, and blood sampling of said mammals.

* * * * *